United States Patent [19]

Hostettler et al.

[11] 4,411,886
[45] Oct. 25, 1983

[54] STABILIZED COSMETIC COMPOSITIONS

[75] Inventors: Hans U. Hostettler, Arlesheim; Horst Beyer, Basel, both of Switzerland

[73] Assignee: Richardson-Vicks Inc., Wilton, Conn.

[21] Appl. No.: 120,208

[22] Filed: Feb. 11, 1980

Related U.S. Application Data

[63] Continuation of Ser. No. 965,003, Nov. 30, 1978, abandoned.

[30] Foreign Application Priority Data

Dec. 9, 1977 [CH] Switzerland .................. 1511277

[51] Int. Cl.³ ............... A61K 7/06; A61K 31/44; A61K 31/00
[52] U.S. Cl. .................. 424/70; 424/DIG. 4; 424/73; 424/168; 424/175; 424/263; 424/358; 424/365
[58] Field of Search ............ 424/70, 73, 168, 175, 424/263, 358, 368, DIG. 4

[56] References Cited

U.S. PATENT DOCUMENTS

| | | | |
|---|---|---|---|
| 3,808,317 | 4/1974 | Hecht et al. | 424/175 |
| 3,890,434 | 6/1975 | Weisse et al. | 424/70 |
| 4,048,181 | 9/1977 | Douglas | 424/DIG. 4 |
| 4,049,665 | 9/1977 | Douglas | 424/DIG. 4 |
| 4,139,635 | 2/1979 | Kalopissis et al. | 424/DIG. 4 |
| 4,152,431 | 5/1979 | Klein | 424/245 |
| 4,163,783 | 8/1979 | Klein et al. | 424/DIG. 4 |

FOREIGN PATENT DOCUMENTS 957458  5/1964  United Kingdom ................ 424/70

OTHER PUBLICATIONS

Chem. Abst. vol . 8, No. 77856p (1974) Edrissi et al.
Chem. Abst., vol. 83, No. 23692e (1975) Evers et al.
Chem. Abst. vol. 82, No. 51359z (1974) Kahn et al.
Chem. Abst., vol. 8, No. 130370m, (1976), Okumura et al.
Chem. Abst., vol. 87, No. 73237p, (1977), Azuna et al.
Chem. Abst., vol. 79, No. 39322n (1973) Weisse.

Primary Examiner—Dale R. Ore
Attorney, Agent, or Firm—Salvatore R. Conte

[57] ABSTRACT

Stabilized cosmetic compositions containing as an active ingredient a compound represented by the formula

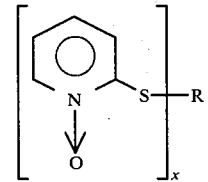

wherein R is sodium, potassium or ammonium and x is 1 or R is aluminum and x is 3. The compounds of the above formula are stabilized in said compositions particularly against degradation due to light by the addition thereto of an effective amount of N-acetylcysteine.

10 Claims, No Drawings

STABILIZED COSMETIC COMPOSITIONS

This is a continuation, of application Ser. No. 965,003 filed Nov. 30, 1978, now abandoned.

BACKGROUND OF THE INVENTION AND STATEMENT OF PRIOR ART

The subject invention pertains to cosmetic compositions containing a compound represented by the formula

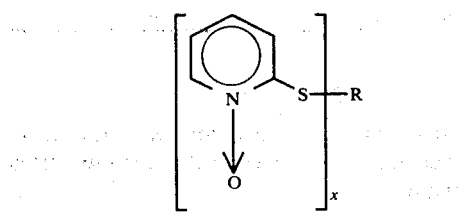

wherein R is sodium, potassium or ammonium and x is 1 or R is aluminum and x is 3.

The compounds of formula I are known compounds and are disclosed in British Pat. No. 957,458 as being useful in cosmetic preparations such as hair lotions, skin creams and the like.

The compounds of formula I, which may be written in a tautomeric form, i.e. "thione-form," are very susceptible to oxidation, particularly in high dilution. Oxidation of the compounds of formula I in solution results in the formation of 2,2'-dithiodipyridine-1,1-dioxide. This susceptability to oxidation has caused problems with the formulation of the compounds of formula I into cosmetic preparations. Since such preparations are normally not stored in a dark place or with the exclusion of light, photochemical oxidation of the compounds of formula I when incorporated therein also presents a significant problem.

The problem of how to stabilize cosmetic preparations containing the compounds of formula I against photodecomposition has been solved in accordance with the present invention by the incorporation therein of an effective amount of N-acetylcysteine. The stabilizing effect of N-acetylcysteine on preparation containing the compounds of formula I is considered unexpected, since N-acetylcysteine exhibits no light absorption over the entire range of the solar spectrum.

STATEMENT OF PRIOR ART

The following references are considered to have pertinency to the subject invention.

U.S. Pat. No. 3,890,434 discloses adducts of bis(2-pyridyl-1-oxide) disulfide with alkaline earth metal salts in hair and antiseptic formulations.

U.S. Pat. No. 3,808,317 discloses compositions of biologically active catechol amines stabilized against degradation by oxidation by an antioxidant combination comprising ascorbic acid and N-acetyl-1-cysteine.

Japan, Kokai, 72/25'312 teaches stabilization of certain preparations containing glutathion with cysteine.

Japan, Kokai, 73/52'767 teaches stabilization of preparations containing 5-hydroxytryptophan with cysteine.

Farmacia (Bucharest) Vol. 23 (4), pp. 205–214, teaches stabilization of vitamin $B_1$-hydrochloride with cysteine.

Taipei Med. Coll. Taipei, Taiwan, Vol. 24 (1), pp. 18–26 (1972), teaches stabilization of certain multivitamin preparations by the addition of cysteine.

DETAILED DESCRIPTION OF THE INVENTION

In accordance with the present invention a method has been discovered whereby cosmetic preparations containing as an active ingredient a compound represented by the general formula

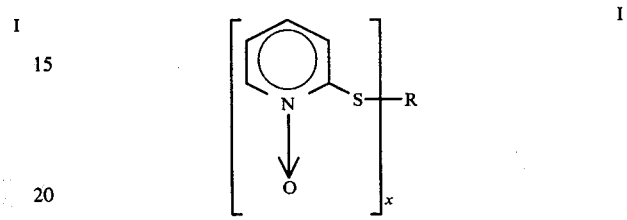

wherein R is sodium, potassium or ammonium and x is 1 or R is aluminum and x is 3.

Such preparations are stabilized in accordance with the present invention by the addition thereto of an effective amount of N-acetylcysteine.

Cosmetic preparations contemplated in accordance with the present invention include, for example, anti-dandruff preparations, skin-care creams, after-shave emulsions and the like. Preparations of this type contain from about 0.005% by weight to about 0.2% by weight, preferably from about 0.05% by weight to about 0.2% by weight of a compound of formula I. The compound of formula I are preferably utilized in anti-dandruff preparations. They can, however, be utilized generally in cosmetic preparations requiring a preservative or disinfectant.

A preferred compound in anti-dandruff preparations in accordance with the present invention is a compound of formula I wherein R is aluminum and x is 3, i.e. aluminum pyridinethione. Aluminum pyridinethione is soluble in a mixture of 3 parts ethanol and 1 part water up to a concentration of 0.7% by weight. Supersaturated solutions in the same vehicle containing up to about 2.5% by weight aluminum pyridinethione can be prepared for ease of incorporation into the cosmetic preparations described herein.

Cosmetic preparations in accordance with the present invention contain N-acetylcysteine in a concentration of from about 0.5 to about 8 times the concentration of the compound of formula I. Preferably, such preparations contain from about 0.01% by weight to about 0.4% by weight, most preferably, from about 0.1% by weight to about 0.4% by weight N-acetylcysteine. Such preparations may, however, contain N-acetylcysteine in a concentration of about 1% by weight or above.

The capability of N-acetylcysteine to prevent photochemical decomposition of cosmetic preparations containing the active ingredients of formula I is readily apparent from the following experiment wherein various preparations were exposed to Xenotest. One hour of Xenotest corresponds to one month of daylight. The results are given in terms of the effectiveness of the stabilization in the following table.

TABLE

| Substance | Active Substance ppm in a hair lotion | | Effectiveness of Stabilization |
|---|---|---|---|
| | N—Acetylcysteine Content | | |
| | — | 0.1% | |
| Aluminum Pyridinethione | | | |
| not exposed | 501 | 505 | |
| 3 hr. Xenotest | 472 | 498 | 79% |
| 6 hr. Xenotest | 467 | 502 | 92% |
| 12 hr. Xenotest | 360 | 491 | 90% |
| In an Ampul | | | |
| not exposed | 501 | 504 | |
| 1 hr. Xenotest | 452 | 484 | 62% |
| 3 hr. Xenotest | 366 | 439 | 53% |
| 6 hr. Xenotest | 239 | 346 | 40% |
| Sodium Pyridinethione | | | |
| not exposed | 500 | 500 | |
| 6 hr. Xenotest | 449 | 487 | 75% |
| 12 hr. Xenotest | 396 | 456 | 58% |
| Potassium Pyridinethione | | | |
| not exposed | 498 | 500 | |
| 6 hr. Xenotest | 447 | 487 | 75% |
| 12 hr. Xenotest | 407 | 460 | 57% |

The results in the table demonstrate the ability of N-acetylcysteine to prevent the degradation of the compounds of formula I in cosmetic preparations as a result of exposure to sunlight.

The following examples further illustrate the invention.

EXAMPLE 1

A stabilized anti-dandruff hair lotion was prepared by conventional techniques from the following formulation.

| Ingredient | Amount |
|---|---|
| D-Panthenol | 5.0 g |
| Aluminum Pyridinethione | 0.5 g |
| N—Acetyl-L-Cysteine | 1.0 g |
| Citric Acid | 1.0 g |
| Triethanolamine | 1.3 g |
| Cremophor RH 60[1] | 0.8 g |
| Alcohol (94% strength) | 300.0 g |
| Perfume | 1.0 g |
| Water, qs ad | 1000.0 ml |

The pH of the preparation was adjusted to 4.5 with triethanolamine.

EXAMPLE 2

A stabilized, unperfumed anti-dandruff hair lotion was prepared by conventional techniques from the formulation of example 1 omitting the perfume and the Cremophor RH 60. The pH was adjusted to pH 7.0 with triethanolamine.

EXAMPLE 3

Stabilized hair lotions were prepared from the formulation of example 2 using in place of the aluminum pyridinethione sodium pyridinethione, potassium pyridinethione and ammonium pyridinethione, respectively.

EXAMPLE 4

A stabilized after-shave emulsion was prepared utilizing conventional techniques from the following formulation.

| Ingredient | Amount of Grams |
|---|---|
| Isopropyl myristate | 15.0 |
| Polyoxyethylene glycol ether of castor oil | 15.0 |
| Hydroxyethyl cellulose | 9.0 |
| dl-α-Tocopherol acetate | 0.5 |
| Perfume | 7.0 |
| D-Panthenolethyl ether | 10.0 |
| Sodium pyridinethione | 1.0 |
| N—Acetylcysteine | 2.0 |
| Water, qs ad | 1000.0 |

EXAMPLE 5

A stabilized oil-in-water emulsion skin-care cream was prepared utilizing conventional techniques from the following formulation.

| Ingredient | Amount of Grams |
|---|---|
| Diethanolamine salt of monocetyl-phosphoric acid | 15.0 |
| Stearic acid | 100.0 |
| Cetyl alcohol | 10.0 |
| Glycerol monomyristate | 50.0 |
| Isopropyl myristate | 80.0 |
| Arachis oil | 40.0 |
| Propylene glycol | 60.0 |
| Sodium pyridinethione | 2.0 |
| N—Acetylcysteine | 2.0 |
| Water, qs ad | 1000.0 |

EXAMPLE 6

A stabilized hair conditioner was prepared by conventional procedures from the following formulation.

| Ingredient | Percent by Weight |
|---|---|
| Cetyl alcohol | 2.00 |
| Colloidally dispersed mixture of cetyl/stearyl alcohol with saturated fatty alcohol polyglycol ethers | 4.00 |
| 2-Octyldodecanol | 2.00 |
| Lauryltrimethylammonium chloride, 35% strength | 3.00 |
| Glycerol | 5.00 |
| Citric Acid | 0.50 |
| Caustic soda solution, 10% to pH 7.0 | |
| N—Acetylcysteine | 0.15 |
| Aluminum pyridinethione | 0.30 |
| Perfume | 0.20 |
| Demineralized water | 82.85 |
| | 100.00 |

We claim:

1. A cosmetic preparation containing, as an active ingredient, an effective amount of a compound represented by the formula

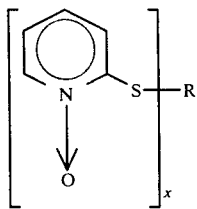

wherein R is sodium, potassium or ammonium and x is 1 or R is aluminum and x is 3 said preparation containing an amount of N-acetylcysteine sufficient to stabilize said compound against photochemical oxidation or decomposition, said N-acetylcysteine being present in from about 0.5 to about 8 times the amount of said compound.

2. A preparation in accordance with claim 1 wherein there is present an amount of N-acetylcysteine equal to about two times the amount of said compound.

3. A preparation in accordance with claim 1 wherein said compound is aluminum pyridinethione.

4. A preparation in accordance with claim 3 wherein said aluminum pyridinethione is present in an amount equal to from about 0.005% by weight to about 0.2% by weight.

5. A preparation in accordance with claim 3 wherein said aluminum pyridinethione is present in an amount equal to from about 0.05% by weight to about 0.2% by weight.

6. A preparation in accordance with claim 1 wherein said preparation is selected from the group consisting of anti-dandruff hair lotions, after-shave emulsion and skin-care cream.

7. A method for the stabilization of a cosmetic preparation which contains, as an active ingredient, an effective amount of a compound represented by the formula

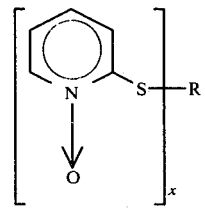

wherein R is sodium, potassium or ammonium and x is 1 or R is aluminum and x is 3 which comprises adding to said preparation an amount of N-acetylcysteine sufficient to stabilize said compound against photochemical oxidation or decomposition said N-acetylcysteine being added in an amount from about 0.5 to about 8 times the amount of said compound.

8. A method in accordance with claim 7 wherein the amount of N-acetylcysteine added to said preparation comprises about two times the amount of said compound present.

9. A method in accordance with claim 7 wherein said compound is aluminum pyridinethione.

10. A method in accordance with claim 10 wherein said aluminum pyridinethione is present in said preparation in an amount equal to from about 0.005% by weight to about 0.2% by weight.

* * * * *